United States Patent [19]

Crossley

[11] 4,183,854
[45] Jan. 15, 1980

[54] THIAZOLE COMPOUND

[75] Inventor: Roger Crossley, Reading, England

[73] Assignee: John Wyeth & Brother Limited, Maidenhead, England

[21] Appl. No.: 929,066

[22] Filed: Jul. 28, 1978

Related U.S. Application Data

[60] Division of Ser. No. 799,911, May 23, 1977, Pat. No. 4,148,904, which is a continuation-in-part of Ser. No. 740,633, Nov. 10, 1976, abandoned.

[51] Int. Cl.² ........................................... C07D 277/20
[52] U.S. Cl. .................................. 548/195; 424/270; 548/200; 548/190; 548/199
[58] Field of Search ................................. 260/306.8 R

[56] References Cited

U.S. PATENT DOCUMENTS

| 3,244,723 | 4/1966 | Johnson et al. | 260/306.8 |
|---|---|---|---|
| 3,850,945 | 11/1974 | Edwards | 260/302 R |
| 3,939,172 | 2/1976 | Gallagher et al. | 260/306.8 R |

OTHER PUBLICATIONS

Johnson et al., J. Org. Chem., vol. 28, 1877–1883, (1963).
Erlenmeyer et al., Helv. Chim. Acta., vol. 29, 1229–1231.

*Primary Examiner*—Nicholas S. Rizzo
*Attorney, Agent, or Firm*—Arthur E. Wilfond

[57] ABSTRACT

The invention relates to pharmaceutical compositions for use in treating ulcers or hypersecretion in mammals comprising a compound of formula Ia

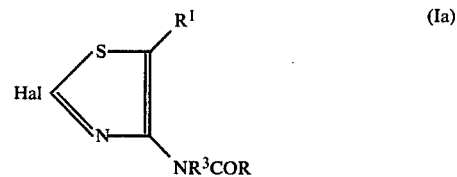

where Hal is a halogen atom, $R^1$ is hydrogen or alkyl of 1–6 carbon atoms, R is hydrogen, alkyl of 1–5 carbon atoms (which may be substituted by two or more chlorine or bromine atoms), alkenyl of 2 to 5 carbon atoms, perfluoroalkyl of 1–5 carbon atoms, cycloalkyl of 3 to 5 carbon atoms, $R^3$ is hydrogen, alkyl of 1–6 carbon atoms, or $COR^4$ where $R^4$ is as defined for R and R and $R^4$ may be the same or different, and a pharmaceutically acceptable carrier.

Methods of treatment of affected mammals and some novel compounds are also described.

3 Claims, No Drawings

THIAZOLE COMPOUND

This is a division, of application Ser. No. 799,911, filed May 23, 1977 now 4,148,904.

This invention relates to novel pharmaceutical compositions with anti-ulcer or anti-secretory activity and methods of treating ulcers or hypersecretion in mammals. Application Ser. No. 799,911 is a continuation-in-part of my copending application Ser. No. 740,633 filed November 10, 1976 now abandoned.

Johnson and Nasutavicus (J. Org. Chem. 1963, 28, 1877–83), have described a new synthesis of 2-bromo-4-amino-thiazoles. In U.S. Pat. No. 3,244,723 the same authors have described thiazoles, including 2-bromo-4-aminothiazoles, with various biological activities namely against fungus, brown root, bean aphid, two spotted spider mite, plum curculio, northern fat-headed mannow and waterplantcoontail.

Some related thiazoles are described in U.S. Pat. No. 3,850,945 (Edwards). This patent is concerned with 2-hydroxyalkoxythiazoles, which 2- substituent is also further substituted, the compounds being said to be useful as cardiovascular agents. In this patent certain 2-halothiazoles are described as intermediates including 2-bromo-4-acetamidothiazole (preparation 12) and 2-chloro-4-formylamino-thiazole (preparation 22).

No pharmaceutical applications of any of these 2-halothiazoles have been reported so far as I am aware. I have now surprisingly found that some 2-bromo-4-acylamino-thiazoles and 2-bromo-4-diacylamino-thiazoles falling within the class of compounds disclosed in these publications have anti-ulcer or anti-secretory activity whereas other closely related compounds are inactive. I have also found that some related 2-chloro-thiazoles have anti-ulcer or anti-secretory activity.

Anti-ulcer activity was determined by the stress-induced erosion test of Senay & Levine, *Proc. Soc. Exp. Biol. Med.* 124, 1221–3(1967) and anti-secretory activity by the test of H. Shay, D. Sun and H. Greenstein, Gastroenterology, 1954, 26, 903–13. The compounds which possess one or both these activities are considered to be anti-ulcer agents which can be used for the treatment of ulcers or hypersecretion in mammals.

The present invention provides a pharmaceutical composition comprising a compound of formula Ia

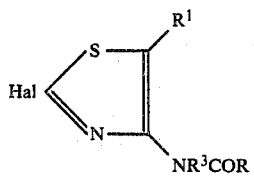

where Hal is a halogen atom, $R^1$ is hydrogen or alkyl of 1-6 carbon atoms, R is hydrogen alkyl of 1-5 carbon atoms (which may be substituted by one or more of the following: trifluoromethyl, methoxy, ethoxy, amino, loweralkylamino, diloweralkylamino, hydroxy, or cyano or by two or more chlorine or bromine atoms), alkenyl of 2 to 5 carbon atoms, alkynyl of 2 to 5 carbon atoms, perfluoroalkyl of 1-5 carbon atoms, cycloalkyl of 3 to 5 carbon atoms, $R^3$ is hydrogen, alkyl of 1-6 carbon atoms, or $COR^4$ where $R^4$ is as defined for R and R and $R^4$ may be the same or different, and a pharmaceutically acceptable carrier.

In the compounds of formula Ia, Examples of R are for the alkyl group methyl, ethyl, n-propyl, isopropyl or n-butyl; for alkenyl group vinyl, prop-1-enyl, but-1-enyl, but-2-enyl; for the alkynyl group ethynyl, prop-2-ynyl, but-2-ynyl; for the cyclo alkyl group cyclopropyl, cyclobutyl and cyclopentyl, for the perfluoroalkyl group, trifluoromethyl and pentafluoroethyl. $R^3$ may be any of the alkyl groups disclosed for R but is preferably methyl.

When the term "lower alkyl" is used in this specification either alone or as part of another radical it means an alkyl group of 1 to 6 carbon atoms which may have a straight or branched chain e.g. methyl, ethyl, n-propyl, iso-propyl, n-butyl, s-butyl, t-butyl, n-pentyl, or n-hexyl. Preferred examples of loweralkylamino are methylamino and ethylamino. Examples of diloweralkyl amino are dimethylamino and diethylamino.

In a preferred aspect the invention provides a pharmaceutical composition for use in the treatment of ulcers or hypersecretion comprising a compound of formula Ia

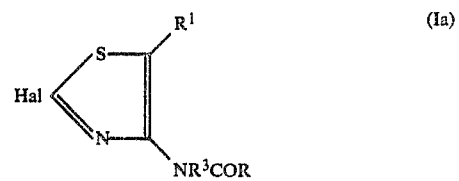

where Hal is a halogen atom, $R^1$ is hydrogen or alkyl of 1-6 carbon atoms, R is hydrogen, or alkyl of 1-5 carbon atoms (which may be substituted by two or more chlorine or bromine atoms), alkenyl of 2 to 5 carbon atoms, perfluoroalkyl of 1-5 carbon atoms, cycloalkyl of 3 to 5 carbon atoms, $R^3$ is hydrogen, alkyl of 1-6 carbon atoms, or $COR^4$ where $R^4$ is as defined for R and R and $R^4$ may be the same or different, and a pharmaceutically acceptable carrier.

$R^1$ when alkyl of 1-6 carbon atoms may be any of the lower alkyl radicals discussed above but is preferably methyl or ethyl. Hal may be chlorine, bromine, fluorine or iodine but preferably is chlorine or bromine.

Preferably the pharmaceutical composition is in unit dosage form e.g. as tablets or capsules.

Many of the compounds of formula I either fall within the generic disclosure or are specifically disclosed in the publications of Johnson and Nasutavicus or Edwards mentioned above.

The pharmaceutical compositions of this invention are distinguished from known insecticidal or anti-fungal compositions or chemical intermediates since these are not formulated to pharmaceutical standards, nor are they in unit dosage forms.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 995 to 99 , preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminium glycinate, calcium carbonate, magnesium trisilicate, sodium bicarbonate or the alumina gel described in British Specification No. 1,284,394.

The preferred compounds of formula Ia used in the pharmaceutical compositions of the invention are those in which Hal is chlorine or bromine, $R^3$ is hydrogen or methyl and R is hydrogen or alkyl of 1-3 carbon atoms preferably methyl. Preferably $R^1$ is hydrogen or methyl. Particularly preferred compounds are 4-acetamido-2-bromothiazole, 4-acetamido-2-bromo-5-methylthiazole, 4-acetamido-2-chlorothiazole, 2-chloro-4-formamidothiazole, and 2-bromo-4-(N-methylacetamido)thiazole.

Another preferred group of compounds used in the pharmaceutical compositions of the invention are those of formula Ia when $R^3$ is $COR^4$ and $R^4$ is hydrogen or alkyl of 1-5 carbon atoms. In these compound preferably R and $R^4$ are both methyl or one of R and $R^4$ is hydrogen and the other is methyl. Compounds of this group where Hal is chlorine or bromine, $R^1$ is hydrogen, and R and $R^4$ are selected from hydrogen and methyl have very good antisecretory activity, e.g. 4-(N-acetyl-N-formyl) amino-2-bromothiazole and 4-diacetylamino-2-bromothiazole.

The compounds of formula Ia wherein $R^3$ is hydrogen or alkyl of 1-6 carbon atoms may be prepared by known methods e.g. by acylation of the corresponding 4-amino-thiazoles or 4-N-alkylaminothiazoles of formula II

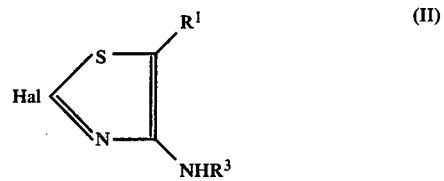

where Hal and $R^1$ are as previously defined and $R^3$ is hydrogen or alkyl of 1-6 carbon atoms.

Standard acylating agents capable of introducing the group RCO may be used e.g. the acid chloride RCOCl, acid anhydride

or mixed anhydride

where R is as defined above and $R^2$ is another R group. Formylation may be carried our using a mixed anhydride of formic and acetic acids. This reagent can be produced from formic acid and acetic anhydride.

When the group R is alkyl carrying a substituent functional group then one such group may be converted to another by standard methods.

Mono formyl compounds of formula Ia where R is hydrogen and $R^3$ is hydrogen may be prepared by treatment of the azide of formula III

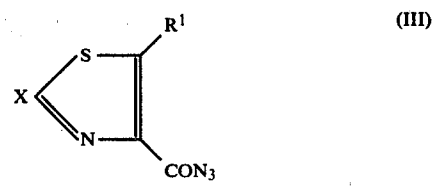

wherein X and $R^1$ are as defined in connection with formula Ia with a formylating agent such as the mixed anhydride of formic and acetic acids.

Thus the azides of formula (III) may be prepared by Curtius rearrangement of a thiazole ester of formula (IV)

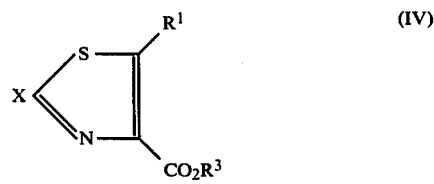

where $R^1$ is as defined in connection with formula Ia and $R^3$ is lower alkyl and X is chlorine or bromine.

The ester of formula (IV) is treated with hydrazine to give the hydrazide of formula (V)

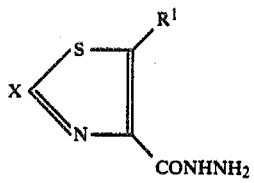

followed by nitrous acid to give the carbonyl azide of formula (III)

The starting compounds of formula II wherein Hal is bromine are described in J. Org. Chem., 1963, 28, 1877-83 or may be prepared by analogous methods. The compounds of formula II where Hal is chlorine may be prepared by methods described by Erlenmeyer et al Helv. Chim. Acta, 29, 1229-31.

Some compounds of formula Ia are known compounds which are described in the two literature references mentioned above or in U.S. Pat. Nos. 3,244,723, or 3,850,945.

Compounds of formula Ia, wherein $R^3$ is $COR^4$ and $R^4$ is hydrogen or alkyl of 1 to 5 carbon atoms e.g. a compound of formula VI

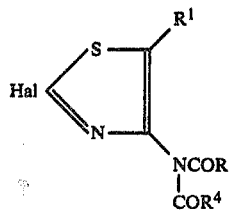

wherein Hal is a halogen atom, and $R^1$ and R are as defined in connection with formula I, may be prepared by acylation of a compound of formula Ia where $R^3$ is hydrogen using an acylating agent containing the group—COR e.g. an acid halide $R^4CO$ Hal where Hal is chlorine or bromine or an anhydride or mixed anhydride. In this way compounds of formula III with different acyl radicals on the nitrogen may be prepared.

When a compound of formula Ia is prepared in which $R^3$ is hydrogen this may be alkylated to give a compound of formula Ia where $R^3$ is alkyl of 1-6 carbon atoms. This alkylation can be carried out by treatment with an alkali metal hydride (e.g. sodium hydride) or equivalent base and an alkylating agent (such as di(-lower alkyl)sulphate, alkyl tosylate or a lower alkyl halide).

Pharmacological Test Results

When tested orally in rats 4-acetamido-2-bromothiazole showed moderate activity at 100 mpk in the test of Senay & Levine mentioned above. The compound displayed outstandingly good anti-secretory activity in the test of Shay et al at 30 and 10 mpk and was also active at 3 mpk. 4-Acetamido-2-bromo-5-methylthiazole was inactive at 100 mpk in the test of Senay & Levine but displayed outstandingly good activity in the anti-secretory test of Shay et al at 30 and 10 mpk.

When tested orally in rats 4-diacetylamino-2-bromothiazole had no significant activity at 100 mpk in the test of Senay & Levine mentioned above. The compound displayed outstandingly good anti-secretory activity in the test of Shay et al at 30 and 10 mpk but was inactive at 3 mpk. 4-Acetamino-2-chlorothiazole displayed outstandingly good activity in the anti-secretory test of Shay et al at 10 mpk and also good activity at 30 mpk and 3 mpk.

Detailed test results are shown in Table I.

TABLE 1

| Compound | Stress-induced erosion (Senay & Levine) | | Anti-secretory (Shay et al) | | | | |
|---|---|---|---|---|---|---|---|
| | mpk p.o. | Inhib | mpk ID | Vol | Conc | Free $H^+$ | Total $H^+$ |
| 4-acetamido-2-bromothiazole | 100 | 54% | 30 | −79% | Insuff. for titration | | |
| | 30 | 40% | 10 | −80% | | | |
| | | | 3 | −42% | −12% NS | −44% | −40% |
| 4-acetamido-2-bromo-5-methyl-thiazole | 50 | NS | 30 | 75% | Insuff. for titration | | |
| | | | 10 | −57% | −44% | −68% | −57% |
| | | | 3 | | Not significant | | |
| 2-bromo-4-iso-butyramidothiazole | 100 | 70% | 30 | | Not significant | | |
| 2-bromo-4-trifluoroacetamido thiazole | 100 | 50% NS | 30 | −31% | −8%NS | −38% | −35% |
| 2-bromo-4-prop-ionamidothiazole | 100 | NS | 30 | −62% | −35% | −70% | −64% |
| | | | 10 | | Not significant | | |
| 2-bromo-4-(cyclo-propylcarboxamido) thiazole | 100 | 70% | 30 | −67% | −34% | −75% | −68% |
| | | | 10 | | Not significant | | |
| 4-diacetylamino-2-bromothiazole | 109 | 29% | 30 | −72% | −22%NS | −71% | −68% |
| | | NS | 10 | −54% | −30% | −66% | −57% |
| | | | 3 | | Not Significant | | |
| 4-acetamido-2-chlorothiazole | 100 | 50% | 30 | −54% | −8%NS | −39%NS | −43% |
| | | | 10 | −79% | −51% | −84% | −79% |
| | | | 3 | −57% | −56% | −78% | −55% |
| 2-bromo-4-n-butyramidothia-zole | 100 | 29% NS | 30 | −34% NS | −20% NS | −42% | −39% |
| 4-acrylamido 2 bromothiazole | 100 | 31% NS | 30 | −29% | −8%NS | −34% | −32% |

TABLE 1-continued

| Compound | Stress-induced erosion (Senay & Levine) | | Anti-secretory (Shay et al) | | | |
|---|---|---|---|---|---|---|
| | mpk p.o. | Inhib | mpk ID | Vol | Conc | Free H+ | Total H+ |
| 2-bromo-4-trichloro-acetamidothiazole | 100 | 36% NS | 30 | −31% | −12% | −39% | −35% |

NS = Not Significant

When tested orally in rats 2-chloro-4-form midothiazole was inactive at 100 mpk in the test of Senay & Levine mentioned above. The compound displayed good anti-secretory activity in the test of Shay et al at 30 and 10 mpk but was inactive at 3 mpk. 4-(N-acetyl-N-formyl)amino-2-bromothiazole showed good activity in the test of Shay et al at 30 mpk.

TABLE 2

| Compound | Stress-induced erosion (Senay & Levine) | | Anti-secretory (Shay et al) | | | |
|---|---|---|---|---|---|---|
| | mpk p.o. | % Inhib | mpk ID | Vol | Conc | Free H+ | Total H+ |
| 2-chloro-4-form-amidothiazole | 100 | 25 | 30 | −53% | −38% | −69% | −60% |
| | | | 10 | −59% | −16% NS | −64% | −60% |
| 2-bromo-4-form-amidothiazole | 100 | Inactive | 100 | −55% | Insufficient gastric juice for titration | | |
| | | | 30 | Inactive | | | |
| 4-(N-acetyl-N-formyl)amino-2-bromothiazole | 100 | Inactive | 30 | −63% | −21% | −68% | −59% |

NS = not significant

When tested orally in rats 2-bromo-4-(N-methylacetamido)thiazole displayed good activity in the test of Shay et al at 30 mpk but weak activity at 10 mpk. It was inactive in the test of Senay & Levine at 30 and 100 mpk.

TABLE 3

| Compound | Anti-secretory (Shay et al) | | | | |
|---|---|---|---|---|---|
| | mpk i.d. | Vol | Conc | Free H+ | Total H+ |
| 2-bromo-4-N-methyl-acetamidothiazole | −30 | −49% | −4% NS | −53% | −37% |
| | −10 | −30% NS | −15% NS | −38% | −31% NS |

NS = Not signficant

The following closely related compounds were inactive in the above tests 4-amino-2-bromothiazole hydrobromide [Senay & Levine (100 mpk) Shay (30 mpk)], 4-amino-2-bromo 5-methylthiazole hydrobromide [Senay & Levine (100 mpk), Shay (30 mpk)], 4-benzamido-2-bromothiazole [Senay & Levine (100 mpk), Shay (30 mpk)], 4-acetamido-2-bromo-5-phenylthiazole [Senay & Levine (100 mpk) Shay (30 mpk)].

The invention includes a method of treating ulcers or hypersection in an afflicted mammal which method comprises administering to said mammal an effective amount of a compound of formula Ia as defined above.

The amount of compound used will depend on the activity of the compound and the needs of the mammal being treated. Doses may range from 3 to 100 mg/kg.

In the pharmaceutical compositions unit doses may vary from 25 to 500 mg. according to the activity of the selected ingredient, preferably 50 to 250 mg. per unit dose.

Preferably the compound used is 4-acetamido-2-bromothiazole, 4-acetamido-2-bromo-5-methylthiazole, 4-acetamido-2-chlorothiazole, 4-diacetamido-2-bromothiazole, 2-chloro-4-formamidothiazole or 4-(N-acetyl-N-formyl)amino-2-bromothiazole.

The following examples illustrate pharmaceutical compositions in accordance with the invention.

EXAMPLE A

| Suspension | % w/v |
|---|---|
| Aluminium hydroxide gel B.P. 5% $Al_2O_3$ | 80% = 4% $Al_2O_3$ |
| Magnesia Magma 12%, w/v MgO | 10% |
| 4-acetamido-2-bromothiazole | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof, 60 O.P. represents 91% w/v Ethanol/Water

The above suspension is prepared by the following procedure. Add to the Alumina gel Magnesia Magma followed by the thiazole dispersed in glycerin, the peppermint oil dissolved in alcohol, the saccharin sodium dissolved in water, and the p-hydroxybenzoates dissolved in water. Make up to volume of water and stir well. Dose 5 ml. t.d.s.

EXAMPLE B

Antacid Tablet (chewable)

| | |
|---|---|
| Saccharin | 1.0 mg. |
| Hydrated alumina sucrose powder | 750.0 mg. |
| 4-acetamido-2-bromothiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE C

Anti-ulcer tablet (without antacid)

| | mg/tablet |
|---|---|
| 4-acetamido-2-bromothiazole | 100 mg. |
| Celutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallised.

EXAMPLE D

A suspension is prepared as described in Example A but replacing 4-acetamido-2-bromothiazole by 4-acetamido-2-bromo-5-methylthiazole.

EXAMPLE E

An antacid tablet is prepared as described in Example B but replacing 4-acetamido-2-bromothiazole by 4-acetamido-2-bromo-5-methylthiazole.

EXAMPLE F

An anti-ulcer tablet is prepared as described in Example C but replacing 4-acetamido-2-bromothiazole by 4-acetamido-2-bromo-5-methylthiazole.

EXAMPLE G

| Suspension | % w/v | |
|---|---|---|
| Aluminium hydroxide gel B.P. 5% $Al_2O_3$ | 80% | = 4% $Al_2O_3$ |
| Magnesia Magma 12% w/v MgO | 10% | |
| 4-diacetylamino-2-bromothiazole | 2.0% | |
| Glycerin B.P. | 3.0% | |
| Alcohol 60 O.P.* | 0.08% | |
| Peppermint oil B.P. | 0.015% | |
| Saccharin sodium B.P. | 0.01% | |
| Methyl p-hydroxybenzoate sodium salt | 0.1% | |
| Propyl p-hydroxybenzoate sodium salt | 0.02% | |

-continued

| Suspension | % w/v |
|---|---|
| Butyl p-hydroxybenzoate sodium salt | 0.01% |
| Water q.s. ad | 100.00% |

*O.P. denotes overproof. 60 O.P. represents 91% w/v Ethanol/Water.

The above suspension is prepared by the following procedure. Add to the Alumina gel, Magnesia Magma followed by the thiazole dispersed in glycerin, the peppermint oil dissolved in alcohol, the saccharin sodium dissolved in water, and the p-hydroxybenzoates dissolved in water. Make up to volume of water and stir well. Dose: 5 ml. t.d.s.

EXAMPLE H

Antacid Tablet (chewable)

| | |
|---|---|
| Saccharine | 1.0 mg. |
| Hydrated alumina sucrose powder | 750.0 mg. |
| 4-diacetylamino-2-bromothiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE I

Anti-ulcer tablet (without antacid)

| | mg/tablet |
|---|---|
| 4-acetamido-2-chlorothiazole | 100 mg. |
| Celutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallised.

EXAMPLE J

A suspension is prepared as described in Example G but replacing 4-diacetylamino-2-bromothiazole by 4-acetamido-2-chlorothiazole.

EXAMPLE K

| Suspension | % w/v | |
|---|---|---|
| Aluminium hydroxide gel B.P. 5% $Al_2O_3$ | 80% | = 4% $Al_2O_3$ |
| Magnesia Magma 12% w/v MgO | 10% | |
| 2-chloro-4-formamidothiazole | 2.0% | |
| Glycerin B.P. | 3.0% | |
| Alcohol 60 O.P.* | 0.08% | |

-continued

| Suspension | % w/v |
|---|---|
| Peppermint oil B.P. | 0.015% |
| Saccharin sodium B.P. | 0.01% |
| Methyl p-hydroxybenzoate sodium salt | 0.1% |
| Propyl p-hydroxybenzoate salt | 0.02% |
| Butyl p-hydroxybenzoate sodium salt | 0.01% |
| Water q.s. ad | 100.00% |

*O.P. denotes overproof, 60 O.P. represents 91% w/v Ethanol/Water.

The above suspension is prepared by the following procedure. Add to the Alumina gel Magnesia Magma followed by the thiazole dispersed in glycerin, the peppermint oil dissolved in alcohol, the saccharin sodium dissolved in water, and the p-hydroxybenzoates dissolved in water. Make up to volume of water and stir well. Dose 5 ml. t.d.s.

EXAMPLE L

Antacid Tablet (chewable)

| | |
|---|---|
| Saccharin | 1.0 mg. |
| Hydrated alumina sucrose powder | 750.0 mg. |
| 2-chloro-4-formamidothiazole | 100.0 mg. |
| Mannitol B.P. | 170.0 mg. |
| Maize starch B.P. dried | 30.0 mg. |
| Talc, purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE M

Anti-ulcer tablet (without antacid)

| | mg/tablet |
|---|---|
| 2-chloro-4-formamidothiazole | 100 mg. |
| Celutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90-2% dextrose. 3-5% maltose remainder higher glucose saccharides. Spray crystallised.

EXAMPLE O

Compositions are prepared as described in Examples K, L or M by replacing 2-chloro-4-formamidothiazole with 4-(N-acetyl-N-formyl)amino-2-bromothiazole.

EXAMPLE P

Compositions are prepared as described in Examples K, L or M by replacing 2-chloro-4-formamidothiazole with 2-bromo-4(N-methylacetamido)thiazole.

PREPARATION OF THE ACTIVE INGREDIENTS

EXAMPLE 1

4-Acetamido-2-bromothiazole

4-Amino-2-bromothiazole hydrobromide (52 g, 0.2 m) was suspended in acetic anhydride (200 ml) then treated dropwise with pyridine (100 ml), maintaining the temperature at 0° C. by means of an ice bath. After the addition was complete, the reaction mixture was stirred for 2 h. at room temperature then poured onto 20% aqueous sodium acetate (2 l.). The solution was cooled, filtered and the precipitate washed with water (2×200 ml.). The product was air dried and recrystalised from acetone to give the title compound (35 g, 80%) m.p. 165° C.

Found: C, 27.5; H, 2.5; N, 12.7. $C_5H_5BrN_2OS$ requires C, 27.2; H, 2.3; N, 12.7%.

EXAMPLE 2

2-Bromo-4-isobutyramidothiazole

A solution of isobutyryl chloride (4.15 ml., 40 mM) in pyridine (50 ml.) was cooled to 0° C. and treated portionwise with 4-amino-2-bromothiazole hydrobromide (7.8 g, 30 mM). After stirring for 1 h. the reaction mixture was poured onto 20% aqueous sodium acetate solution (500 ml) and extracted with chloroform (3×200 ml.). The combined organic layers were dried and the solvents removed under reduced pressure to yield an oil which eventually crystallised. Recrystallisation from 60°-80° petroleum ether gave the title compound (2 g, 20%). mp: 95° (Found: C, 34.1; H, 3.8; N, 11.3. $C_7H_9BrN_2OS$ requires C, 33.7; H, 3.6; N, 11.2%).

EXAMPLE 3

4-Acetamido-2-bromo-5-methylthiazole

A suspension of 4-amino-2-bromo-5-methylthiazole hydrobromide (50 mM 13.7 g) in acetic anhydride (100 ml.) was treated dropwise with pyridine (10 ml.) while cooling in an ice bath. After stirring for 1 hr. the reaction mixture was poured onto 20% aqueous sodium acetate (1l.) and the aqueous solution extracted with dichloromethane (3×500 ml.). The combined organic layers were dried and evaporated under reduced pressure to give an oil which crystallised on trituration with ether. The crude product was recrystallized from ethanol to give the title compound (11.7 g, 50%). mp 129° (Found: C, 31.15; H, 3.15; N, 12.3. $C_6H_7BrN_2OS$ requires: C, 30.6; H, 3.0; N, 11.9%).

EXAMPLE 4

2-Bromo-4-trifluoroacetamidothiazole

4-Amino-2-bromothiazole hydrobromide (19.5 g, 75 mM) was suspended in trifluoroacetic anhydride (200 ml.) and dichloromethane (200 ml.). The mixture was cooled to 0° C. and treated dropwise with pyridine (50 ml.). After the addition was complete the mixture was stirred for 1 hour at room temperature, then poured onto a mixture of ice cold 20% aqueous sodium acetate solution (1l.) and dichloromethane (500 ml.). The layers were separated and the aqueous layer extracted with dichloromethane (500 ml.). The combined organic layers were dried ($MgSO_4$) and the solvent removed under reduced pressure. Distillation of the residue gave the title compound (18 g, 87%) b.p. 90°-95° C. at 0.3 mm as an oil which subsequently solidified. Sublimation (50°–60° C. at 0.01 mm) gave analytically pure material mp. 71° C. (Found: C, 22.1; H, 0.8; N, 10.2. $C_5H_2ON_2BrF_3S$ requires: C, 21.8; H, 0.7; N, 10.2%).

EXAMPLE 5

2-Bromo-4-propionamidothiazole

4-Amino-2-bromothiazole hydrobromide (6.5g.) was suspended in propionic anhydride (25 ml.) with stirring; then treated with pyridine (12.5 ml.) over 15 minutes, maintaining reaction temperature at 0° C. with an ice bath. After the addition was complete, the reaction mixture was stirred for 2 hours at room temperature, then poured onto 20% aqueous sodium acetate (250 ml.) and stirred for 30 minutes. The precipitate was removed by filtration and washed with water. The solid was air dried and extracted with hexane, in a Sexhlet apparatus. The hexane was cooled and the crystals collected and recrystallised to give the title compound (2.8 g.) m.p. 122°–5° C. (Found: C, 31.1; H, 3.1; N, 11.9. $C_6H_7BrN_2OS$ requires C, 30.7; H, 3.0; N, 11.9%).

EXAMPLE 6

2-Bromo-4-(cyclopropylcarboxamido)thiazole

4-Amino-2-bromothiazole hydrobromide (15.6 g.) and cyclopropylcarbonyl chloride (8.2 g.) were suspended in methylene chloride (100 ml.) with stirring and treated with pyridine (16 ml.) maintaining reaction temperature at 0° C. with an ice bath. After completing the addition, the reaction mixture was stirred at room temperature for 3 hours, then poured onto 20% aqueous sodium acetate and stirred for 30 minutes. The mixture was separated and the organic layer washed with 2N hydrochloric acid, water, sodium carbonate solution and water. The organic layer was dried and the solvent removed in vacuo and the residue recrystallised three times from carbon tetrachloride to give the title compound (7.3 g) m.p. 152°–3° C. (Found: C, 34.7; H, 3.0; N, 11.4. $C_7H_7BrN_2OS$ requires C, 34.0; H, 2.9; N, 11.3%).

EXAMPLE 7

4-Diacetylamino-2-bromothiazole

A solution of 4-acetylamino-2-bromothiazole 10g, prepared as described in Example 1, in acetic anhydride (100 ml) and pyridine (35 ml) was stirred at 100° C. for 24 hours. The reaction mixture was cooled and the excess acetic anhydride and pyridine removed in vacuo, and the residue was re-evaporated three times with toluene. The residue was purified by column chromatography using silica gel and eluting with chloroform, and recrystallised from hexane to give the title compound (1.2 g) m.p. 63°–65° C. (Found: C, 32.1; H, 2.8; H, 10.6 $C_7H_7BrN_2O_2S$ requires C, 32.0; H, 2.7; N, 10.7%)

EXAMPLE 8

2-Bromo-4-(n-butyramido)thiazole

4-Amino-2-bromothiazole hydrobromide (15.6g) and n-butyryl chloride (8.3g) were suspended in methylene chloride (100 ml) with stirring and treated with pyridine (16ml.) over 15 minutes; maintaining reaction temperatures at 0° C. with an ice bath. After the addition was complete, the reaction mixture was stirred at room temperature for 3 hours, then poured onto 20% aqueous sodium acetate (500 ml) and stirred for 30 minutes. The mixture was separated and the organic layer washed with 2N hydrochloric acid, water, sodium carbonate solution and water. The organic layer was dried ($MgSO_4$) and the solvent removed in vacuo and the residue recrystallised twice from carbon tetrachloride and once from methanol to give the title compound (3g). m.p. 119°–20° C. (Found: C, 34.3; H, 3.7; N, 11.2. $C_7H_9BrN_2OS$ requires C, 33.8; H, 3.6; N, 11.3%).

EXAMPLE 9

4-Acrylamido-2-bromothiazole

4-Amino-2-bromothiazole hydrobromide (15.6g) and acryloylchloride (7g) were suspended in methylene chloride (100 ml) with stirring and treated with pyridine (16 ml.), maintaining reaction temperature at 0° C. with an ice bath. After addition was complete, the reaction mixture was stirred at room temperature for 3 hours, then poured onto 20% aqueous sodium acetate and stirred for 30 minutes. The mixture was filtered and separated and the organic layer washed with 2N hydrochloric acid, water, sodium carbonate solution and water. The organic layer was dried ($MgSO_4$) and the solvent removed in vacuo. The residue was recrystallised from carbon tetrachloride to give the title compound (0.7 g) m.p. 152°–4° C. (Found: C, 30.5; H, 2.2; N, 11.8. $C_6H_5BrN_2OS$ requires C, 30.9; H, 2.2; N, 12.0%).

EXAMPLE 10

2-Bromo-4-trichloroacetamidothiazole

4-Amino-2-bromo-thiazole hydrobromide (15.6g) and trichloroacetyl chloride (14.3 g) were suspended in methylene chloride (100 ml) with stirring and treated dropwise with pyridine (16 ml) over 15 minutes maintaining reaction temperatures at 0° C. with an ice bath. After completing the addition, the reaction mixture was stirred at room temperature for 3 hours, then poured onto 20% aqueous sodium acetate (250 ml.) and stirred for 30 minutes. The mixture was separated and the organic layer washed with 2N hydrochloric acid, water, sodium carbonate solution and water. The organic layer was dried ($MgSO_4$) and the solvent removed in vacuo and the residue treated with charcoal in hexane and recrystallised from hexane to give the title compound (10.5g) m.p. 77°–80° C. (Found: C, 19.0; H, 0.7 N, 8.5. $C_5H_2Cl_3BrN_2OS$ requires C, 18.5; H, 0.6; N, 8.6%)

EXAMPLE 11

4-Acetamido-2-chlorothiazole

A solution of 2-chlorothiazole-4-carbonylazide (1) (2g) in a mixture of acetic anhydride (12 ml) and acetic acid (4 ml) was heated on a steam bath for 1 hour then cooled and filtered. The precipitate was purified to give the bis-thiazolylurea (2).

The filtrate was evaporated under reduced pressure and the residue was dissolved in ethanol and re-evaporated. The residue was sublimed twice under reduced pressure (14mm, 120° C.) to give the title compound (500mg, 20%) m.p. 153° C. (Found: C, 33.9; H, 2.85; N, 15.8%. $C_5H_5ClN_2OS$ requires: C, 34.0; H, 2.85; N, 15.9%).

(1) A suspension of 2-chlorothiazole-4-carbohydrazine prepared as described in Helv. Chim. Acta 29 1946 1229 (4.5g, 25mM) in water (35 ml) was treated with hydrochloric acid (9ml), cooled to 0° C. then treated dropwise with a solution of sodium nitrite (2.25g) in water (7.5ml). Strong cooling was required to maintain the internal temperature in the range 0° to 5° C. After 15 minutes the product was removed by filtration, washed with cold water (10 ml) and air dried. Recrystallisation from hexane (with charcoal treatment) gave 2-chlorothiazole-4-carbonylazide (2g, 42%) mp >250° (d).

(2) The azide (2g) was dissolved in a mixture of acetic anhydride (12 ml) and acetic acid (4 ml) and the mixture heated on a steam bath for 1 hour. After cooling, the product was removed by filtration and recrystallised from ethanol to give N,N'-bis-2-chloro-4-thiazolylurea compound (0.5g, 15%) mp: 250° C. (d). (Found: C, 28.8; H, 1.6; N, 18.8% C$_7$H$_4$Cl$_2$N$_4$OS$_2$ requires: C, 28.5; H, 1.4; N, 19.0%)

From the acetic anhydride/acetic acid mother liquors 4-Acetamido-2-chlorothiazole was isolated as described above.

EXAMPLE 12

2-Chloro-4-formamidothiazole (a) 2-Chlorothiazole-4-carbonylazide

A suspension of 2-chlorothiazole-4-carbohydrazine prepared as described in Helv.Chim.Acta 29 (1946) 1229 (4.5g, 25mM) in water (35 ml) was treated with hydrochloric acid (9 ml.), cooled to 0° C. then treated dropwise with a solution of sodium nitrite (2.25g) in water (7.5 ml.). Strong cooling was required to maintain the internal temperature in the range 0° to 5° C. After 15 minutes the product was removed by filtration, washed with cold water (10 ml) and air dried. Recrystallisation from hexane (with charcoal treatment) gave 2-chlorothiazole-4-carbonylazide (2g, 42%) mp >250° (d).

(b) 2-Chloro-4-formamidothiazole

99% Formic acid (50 ml) was added slowly to acetic anhydride (100 ml.) with cooling, then the mixture was heated at 50° C. for 15 minutes. The mixture was cooled to 0° C. to give a solution of formic-acetic anhydride in acetic acid.

2-Chlorothiazole-4-carboxylazide (2g) was dissolved in the formic-acetic anhydride solution (20 ml) and the solution was heated for 1 hour on a steam bath. The solvents were removed under reduced pressure and the residue evaporated twice with ethanol. The residue was sublimed twice under reduced pressure (14 mm/120° C.) to give the title compound (800mg, 50%) m.p. 138° C. (Found: C, 29.7; H, 1.95; H, 17.1% C$_4$H$_3$ClN$_2$OS requires: C, 29.6; H, 1.8; N, 17.2%).

EXAMPLE 13

2-Bromo-4-formamidothiazole

Acetic anhydride (100 ml.) was cooled to 0° C. and treated with 98% formic acid (50 ml.). The resulting mixture was heated at 50° C. for 15 minutes then cooled to 0° C. To this solution of formic-acetic anhydride was added 4-amino-2-bromothiazole hydrobromide (26 g, 0.1 m) followed dropwise by pyridine (25 ml.). The reaction mixture was allowed to stand for 1 hour at room temperature then poured onto 20% aqueous sodium acetate solution (500 ml.). The resulting cyrstals were removed by filtration, washed once with water (100 ml.) then recrystallised from ethanol to give the 2-bromo-4-formamidothiazole (12 g, 58%). m.p. 167° C. d. (Found: C, 23.55; H, 1.6; N, 13.45. C$_4$H$_3$N$_2$BrOS requires C, 23.2; H, 1.45; N, 13.5%).

EXAMPLE 14

2-Bromo-4-formamido-5-methylthiazole

4-Amino-2-bromo-5-methylthiazole is treated with formic-acetic anhydride (prepared as described in Example 12b) to give the title compound.

EXAMPLE 15

4-(N-acetyl-N-formyl)amino-2-bromothiazole

4-Acetamido-2-bromothiazole (prepared as described in Example 1) is treated with formic-acetic anhydride to give the title compound.

EXAMPLE 16

4-(N-Acetyl-N-formyl)amino-2-bromothiazole

A solution of 2-bromo-4-formamidothiazole (2.07g, 10mM) and acetyl chloride (8 ml) in ethylene dichloride (200 ml.) was stirred at 60° C. for 24 hours in the presence of powdered 4A molecular sieve (45g). The reaction mixture was cooled to ambient temperature and filtered. The filtrate was evaporated under reduced pressure and then residue triturated with toluene (20 ml.). The solution was filtered, the filtrate evaporated and the residue recrystallised from diethyl ether at −78° to give the title compound (600 mg, 24%) m.p. 62°. (Found: C, 29.3; H, 2.1; N, 11.3%. C$_6$H$_5$N$_2$BrO$_2$S requires C, 28.9; H, 2.0; N, 11.1%).

EXAMPLE 17

2-Bromo-4-(N-methylacetamido)thiazole

A solution of 4-acetamido-2-bromothiazole (prepared as described in Example 1) and methyl tosylate (4.65g, 25mM) in dry acetonitrile (125 ml.) was treated with a 60% dispersion of sodium hydride in oil (1g, 25mM) and the mixture stirred 72 hours at ambient temperature. The reaction mixture was filtered and the filtrate evaporated under reduced pressure. The residue was chromatographed on silica (Woelm grade 1, 150g) using 2% methanol in chloroform as eluant. Evaporation of the appropriate fractions followed by recrystallisation from hexane gave the title compound (1.9g, 32%) mp 84° C. Found: C, 30.55; H, 2.95; N, 11.8%. C$_6$H$_7$N$_2$BrOS requires C, 30.7; H, 3.0; N,.11.9%).

The invention includes a compound of formula I

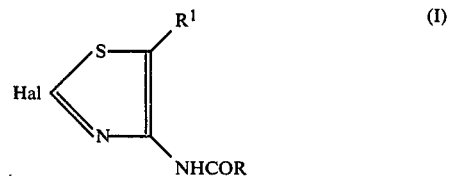

where Hal is chlorine or bromine, R$^1$ is hydrogen or methyl and R is ethenyl or cyclopropyl.

Preferred compounds of formula I are 4-acrylamido2-bromothiazole and 2-bromo-4-(cyclopropylcarboxamido)thiazole.

The above compounds of formula I may be prepared by methods given above.

I claim:

1. A compound of formula I

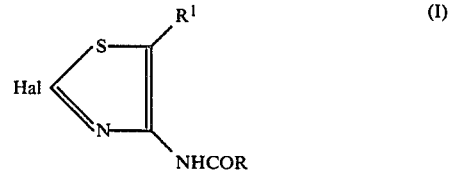

where Hal is chlorine or bromine, R$^1$ is hydrogen or methyl and R is ethenyl or cyclopropyl.

2. A compound as claimed in claim 1 which is 4-acrylamido-2-bromothiazole.

3. A compound as claimed in claim 1 which is 2-bromo-4-(cyclopropylcarboxamido)thiazole.

* * * * *